United States Patent
Levin et al.

(10) Patent No.: US 8,281,675 B2
(45) Date of Patent: Oct. 9, 2012

(54) DISSOLUTION RATE VERIFICATION

(75) Inventors: Galit Levin, Nordiya (IL); Meir Stern, Rehovot (IL)

(73) Assignee: Syneron Medical Ltd, Yokneam Illit (IL)

( * ) Notice: Subject to any disclaimer, the term of this patent is extended or adjusted under 35 U.S.C. 154(b) by 248 days.

(21) Appl. No.: 12/676,983

(22) PCT Filed: Oct. 22, 2008

(86) PCT No.: PCT/IL2008/001389
§ 371 (c)(1), (2), (4) Date: May 3, 2010

(87) PCT Pub. No.: WO2009/050718
PCT Pub. Date: Apr. 23, 2009

(65) Prior Publication Data
US 2010/0229636 A1 Sep. 16, 2010

Related U.S. Application Data

(60) Provisional application No. 60/999,512, filed on Oct. 17, 2007.

(51) Int. Cl.
*G01N 33/00* (2006.01)
(52) U.S. Cl. .......................................................... 73/866
(58) Field of Classification Search .................. None
See application file for complete search history.

(56) References Cited

U.S. PATENT DOCUMENTS

| | | | |
|---|---|---|---|
| 3,801,280 A | 4/1974 | Shah et al. | |
| 4,335,438 A | 6/1982 | Smolen | |
| 4,578,244 A | 3/1986 | Cosgrove, Jr. et al. | |
| 4,593,563 A | 6/1986 | Laine et al. | |
| 5,141,750 A | 8/1992 | Lee et al. | |
| 5,230,898 A | 7/1993 | Horstmann et al. | |
| 5,318,514 A | 6/1994 | Hofmann | |
| 5,380,272 A | 1/1995 | Gross | |
| 5,445,609 A | 8/1995 | Lattin et al. | |
| 5,445,611 A | 8/1995 | Eppstein et al. | |
| 5,458,140 A | 10/1995 | Eppstein et al. | |
| 5,681,282 A | 10/1997 | Eggers et al. | |
| 5,685,837 A | 11/1997 | Horstmann | |
| 5,698,217 A | 12/1997 | Wilking | |

(Continued)

FOREIGN PATENT DOCUMENTS

EP 0 547 482 B2 6/1993

(Continued)

OTHER PUBLICATIONS

An Office Action dated Sep. 8, 2010 which issued during the prosecution of Applicant's European Patent Application No. 99 952 784.9.

(Continued)

*Primary Examiner* — Robert R Raevis
(74) *Attorney, Agent, or Firm* — Smith Risley Tempel Santos LLC; Gregory Scott Smith

(57) ABSTRACT

Apparatus (50) is described for use with a drug on a drug patch (28), the drug patch including a drug side and a back side. An absorbent material (54) is configured to be disposed on a surface (56) and underneath the drug patch. A squeezing device (52) having a squeezing surface is configured to squeeze the drug patch together with the absorbent material. Other embodiments are also described.

23 Claims, 1 Drawing Sheet

U.S. PATENT DOCUMENTS

| | | | |
|---|---|---|---|
| 5,722,397 A | 3/1998 | Eppstein | |
| 5,827,984 A * | 10/1998 | Sinnreich et al. | 73/866 |
| 5,885,211 A | 3/1999 | Eppstein et al. | |
| 5,983,135 A | 11/1999 | Avrahami | |
| 6,022,316 A | 2/2000 | Eppstein et al. | |
| 6,142,939 A | 11/2000 | Eppstein et al. | |
| 6,148,232 A | 11/2000 | Avrahami | |
| 6,173,202 B1 | 1/2001 | Eppstein | |
| 6,183,434 B1 | 2/2001 | Eppstein | |
| 6,248,349 B1 | 6/2001 | Suzuki et al. | |
| 6,251,100 B1 | 6/2001 | Flock et al. | |
| 6,352,506 B1 | 3/2002 | Eppstein et al. | |
| 6,374,136 B1 | 4/2002 | Murdock | |
| 6,508,785 B1 | 1/2003 | Eppstein | |
| 6,522,918 B1 | 2/2003 | Crisp et al. | |
| 6,527,716 B1 | 3/2003 | Eppstein | |
| 6,530,915 B1 | 3/2003 | Eppstein et al. | |
| 6,597,946 B2 | 7/2003 | Avrahami et al. | |
| 6,611,706 B2 | 8/2003 | Avrahami et al. | |
| 6,692,456 B1 | 2/2004 | Eppstein et al. | |
| 6,708,060 B1 | 3/2004 | Avrahami et al. | |
| 6,711,435 B2 | 3/2004 | Avrahami | |
| 6,855,372 B2 | 2/2005 | Trautman et al. | |
| 6,929,782 B1 | 8/2005 | Ciliberto et al. | |
| 6,932,983 B1 | 8/2005 | Straub et al. | |
| 7,021,163 B2 * | 4/2006 | Kyne | 73/866 |
| 7,024,955 B2 | 4/2006 | Carlson et al. | |
| 7,062,317 B2 | 6/2006 | Avrahami et al. | |
| 7,097,850 B2 | 8/2006 | Chappa et al. | |
| 7,123,957 B2 | 10/2006 | Avrahami | |
| 7,164,942 A2 | 1/2007 | Avrahami et al. | |
| 7,237,436 B2 | 7/2007 | Tian et al. | |
| 7,335,377 B2 | 2/2008 | Stern et al. | |
| 7,363,075 B2 | 4/2008 | Stern et al. | |
| 7,383,084 B2 | 6/2008 | Stern et al. | |
| 7,395,111 B2 | 7/2008 | Levin et al. | |
| 7,415,306 B2 | 8/2008 | Levin et al. | |
| 7,558,625 B2 | 7/2009 | Levin et al. | |
| 2001/0051180 A1 | 12/2001 | Watanabe et al. | |
| 2002/0010412 A1 | 1/2002 | Eppstein | |
| 2002/0091311 A1 | 7/2002 | Eppstein et al. | |
| 2002/0099308 A1 | 7/2002 | Bojan et al. | |
| 2002/0169394 A1 | 11/2002 | Eppstein et al. | |
| 2003/0078499 A1 | 4/2003 | Eppstein | |
| 2003/0092982 A1 | 5/2003 | Eppstein | |
| 2003/0204163 A1 | 10/2003 | Marchitto et al. | |
| 2004/0039342 A1 | 2/2004 | Eppstein et al. | |
| 2004/0039343 A1 | 2/2004 | Eppstein et al. | |
| 2004/0059282 A1 | 3/2004 | Flock et al. | |
| 2004/0115822 A1 | 6/2004 | Schapaugh et al. | |
| 2004/0137044 A1 | 7/2004 | Stern et al. | |
| 2005/0119605 A1 | 6/2005 | Sohn | |
| 2005/0238540 A1 * | 10/2005 | Swon et al. | 422/99 |
| 2007/0031495 A1 | 2/2007 | Eppstein et al. | |
| 2007/0141132 A1 | 6/2007 | Sacks et al. | |
| 2007/0270732 A1 | 11/2007 | Levin et al. | |
| 2007/0287949 A1 | 12/2007 | Levin et al. | |
| 2007/0292445 A1 | 12/2007 | Levin | |
| 2008/0114281 A1 | 5/2008 | Birchall et al. | |
| 2008/0208107 A1 | 8/2008 | McRae et al. | |
| 2008/0274166 A1 | 11/2008 | Sacks et al. | |
| 2009/0264810 A1 | 10/2009 | Eppstein et al. | |
| 2010/0174224 A1 | 7/2010 | Sohn | |
| 2010/0293807 A1 | 11/2010 | Bar-El et al. | |

FOREIGN PATENT DOCUMENTS

| | | |
|---|---|---|
| WO | 89/06555 A1 | 7/1989 |
| WO | 94/14062 A1 | 6/1994 |
| WO | 96/00111 A1 | 1/1996 |
| WO | 96/17651 A1 | 6/1996 |
| WO | 96/40364 A1 | 12/1996 |
| WO | 97/07734 A1 | 3/1997 |
| WO | 97/16222 A1 | 5/1997 |
| WO | 98/00193 A1 | 1/1998 |
| WO | 98/29134 A2 | 7/1998 |
| WO | 99/44507 A1 | 9/1999 |
| WO | 99/44508 A1 | 9/1999 |
| WO | 99/44637 A1 | 9/1999 |
| WO | 99/44638 A1 | 9/1999 |
| WO | 99/44678 A1 | 9/1999 |
| WO | 00/03758 A1 | 1/2000 |
| WO | 00/04832 A1 | 2/2000 |
| WO | 00/15102 A1 | 3/2000 |
| WO | 00/59371 A1 | 10/2000 |
| WO | 00/74583 A1 | 12/2000 |
| WO | 00/74767 A2 | 12/2000 |
| WO | 00/76575 A2 | 12/2000 |
| WO | 01/35820 A1 | 5/2001 |
| WO | 02/090210 A1 | 11/2002 |
| WO | 03/039620 A2 | 5/2003 |
| WO | 03/077970 A2 | 9/2003 |
| WO | 03/077971 A2 | 9/2003 |
| WO | 03/101507 A2 | 12/2003 |
| WO | 2005/088299 A1 | 9/2005 |
| WO | 2006/131931 A2 | 12/2006 |
| WO | 2008/091878 A1 | 7/2008 |
| WO | 2009/047774 A2 | 4/2009 |
| WO | 2009/050718 A2 | 4/2009 |

OTHER PUBLICATIONS

An Examination Report dated Aug. 11, 2008, which issued during the prosecution of Applicant's European Patent Application No. 99 952 784.9.

Supplementary European Search Report dated Apr. 29, 2011 issued during prosecution of EP 06 75 6211.

European Search Report dated Apr. 7, 2011 issued during prosecution of Ep 11 00 0062.

Examination Report dated Apr. 6, 2011 issued during prosecution of EP 99952784.9.

Parul B. Patel, et al; "Fast Dissolving Drug Delivery Systems: An Update", Jul. 2, 2006, Pharmainfo.net, 22 pages.

Martin Siewert, et al; FIP/AAPS Guidelines to Dissolution/in Vitro Release Testing of Novel/Special Dosage Forms:, AAPS PharmSciTech, Jan. 27, 2003; 4(1), Article 7, http://www.pharmscitech.org, pp. 1-10.

Galit Levin, et al; "Transdermal Delivery of Human Growth Hormone Through RF-Microchannels", Pharmaceutical Research, vol. 22, No. 4, Apr. 2005, pp. 550-555, Epub 2005 Apr. 7.

International Search Report: mailed Feb. 5, 2009; PCT/IL2008/001389.

International Preliminary Report on Patentability dated Apr. 29, 2010; PCT/IL08/001389.

* cited by examiner

DISSOLUTION RATE VERIFICATION

CROSS-REFERENCES TO RELATED APPLICATIONS

The present application is a U.S. national phase of PCT Application No. PCT/IL2008/001389 to Levin et al., filed Oct. 22, 2008, which claims the benefit of U.S. Provisional Patent Application 60/999,512 to Levin et al., filed Oct. 17, 2007, entitled, "Dissolution rate verification," which is incorporated herein by reference.

FIELD OF THE INVENTION

The present invention generally relates to medical apparatus and methods. Specifically, the present invention relates to dissolvable drug patches.

BACKGROUND OF THE INVENTION

In recent years many drugs have been formulated for transdermal delivery. Transdermal delivery of drugs is the favored delivery method for many patients, particularly for those who find it difficult to have drugs administered to them orally or via an injection.

US Patent Application Publication 2004/0137044 to Stern et al., which is incorporated herein by reference, describes a system for transdermal delivery of dried or lyophilized pharmaceutical compositions and methods for using the system. The system comprises an apparatus for facilitating transdermal delivery of an agent that generates hydrophilic microchannels, and a patch comprising a therapeutically active agent. The system is described as being useful for transdermal delivery of hydrophilic agents, particularly of high molecular weight proteins.

U.S. Pat. No. 5,983,135 to Avrahami, which is incorporated herein by reference, describes a device for delivery of a powder to the skin of a subject which includes a pad, made of an insulating material and having an upper side and a lower side, which lower side is placed against the skin after application of the powder thereto. An electrical power source applies an electrical potential to the pad, causing the powder to adhere by electrostatic force to the lower side of the pad, and then alters the potential so that the powder is released from the pad and contacts the skin against which the pad is placed.

U.S. Pat. No. 7,097,850 to Chappa et al., relevant portions of which are incorporated herein by reference, describes a coating composition in the form of a one or multi-part system, and method of applying such a composition under conditions of controlled humidity, for use in coating device surfaces to control and/or improve their ability to release bioactive agents in aqueous systems. The coating composition is particularly adapted for use with medical devices that undergo significant flexion and/or expansion in the course of their delivery and/or use, such as stents and catheters. The composition includes the bioactive agent in combination with a first polymer component such as polyalkyl(meth)acrylate, polyaryl(meth)acrylate, polyaralkyl(meth)acrylate, or polyaryloxyalkyl(meth)acrylate and a second polymer component such as poly(ethylene-co-vinyl acetate).

U.S. Pat. No. 6,932,983 to Straub et al., relevant portions of which are incorporated herein by reference, describes drugs, especially low aqueous solubility drugs, which are provided in a porous matrix form, preferably microparticles, which enhances dissolution of the drag in aqueous media. The drug matrices preferably are made using a process that includes (i) dissolving a drug, preferably a drug having low aqueous solubility, in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution to yield the porous matrix of drug. The pore forming agent can be either a volatile liquid that is immiscible with the drag solvent or a volatile solid compound, preferably a volatile salt. In a preferred embodiment, spray drying is used to remove the solvents and the pore forming agent. The resulting porous matrix is described as having a faster rate of dissolution following administration to a patient, as compared to non-porous matrix forms of the drug. In a preferred embodiment, microparticles of the porous drug matrix are reconstituted with an aqueous medium and administered parenterally, or processed using standard techniques into tablets or capsules for oral administration.

U.S. Pat. No. 4,335,438 to Smolen, relevant portions of which are incorporated herein by reference, describes a method and apparatus for performing dissolution testing of pharmaceutical dosage forms, agricultural products, and components of industrial products, wherein the method uses dissolution profiles from a known drug dosage form, or product, as reference data for a predictive process, and the apparatus is organized to carry out the method via both closed loop and open loop operating modes under the control of a central processor. An illustrative embodiment describes the serial usage of the two operating modes in a single flow-through dissolution cell configuration to predict the time course of in vivo bioavailability from in vitro dissolution measurements, while an alternate embodiment describes the use of a plurality of dissolution cells and the simultaneous use of the closed and open loop operating modes to implement an Internal Standard capability. Additionally, an adaptive capability is provided in the dissolution testing process via a random input modeling mode of operation.

U.S. Pat. No. 7,024,955 to Carlson et al., relevant portions of which are incorporated herein by reference, describes methods and systems for determining a dissolution profile of a sample material, and for solubilization screening of a library defined by an array comprising multiple sample materials. The methods and systems are described as being suitable for sampling and evaluation of very small samples, and for evaluation of drug candidates.

U.S. Pat. No. 4,593,563 to Laine et al., relevant portions of which are incorporated herein by reference, describes a method and apparatus for accurately determining the rate of dissolution of solid substances. The method and apparatus are directed to a system wherein a sample of solid, which may be powdery, is placed in a sample holder which is then immersed in a perfusion chamber. The weight of the sample is measured as a function of time as the sample dissolves. The sample holder is described as having a variable internal volume which adjusts to the amount of sample therein so as to maintain a substantially constant liquid/solid interface area during dissolution rate measurements.

U.S. Pat. No. 7,237,436 to Tian et al., relevant portions of which are incorporated herein by reference, describes a device and methods for dissolution or immersion testing and, in particular, a device and methods that limit the ability of pharmaceutical or other dosage forms to move or reorient during testing.

U.S. Pat. No. 3,801,280 to Shah et al., relevant portions of which are incorporated herein by reference, describes an apparatus and method for measuring the dissolution rate of a solid material. A container is provided for a solvent and a perforated chamber for the solid material is positioned within the container. A rotatable hollow filter is also located within the container and means are provided for effecting rotation thereof. The rotation performs the double function of keeping the filter screen clear of solid particles and agitating the solvent. Pumping means draw the material-containing solution from within the hollow filter and convey it to suitable means for measuring the concentration of solute in the solvent, such as spectrographic measuring means. The material-containing solution may then be returned to the container.

US Patent Application Publication 2007/0141132 to Sacks et al., which is incorporated herein by reference, describes a transdermal patch formulation comprising human growth hormone (hGH), at least one sugar, one amino acid or polyol, and a buffer, wherein the buffer maintains the pH of the formulation in the range of about 5 to about 9 and the formulation does not contain both glycine and mannitol.

An article entitled, "FIP/AAPS guidelines to dissolution/in vitro release testing of novel/special dosage forms," by Siewert et al., AAPS PharmSciTech 2003; 4 (1) Article 7, relevant portions of which are incorporated herein by reference, states that dissolution testing is a very important tool in drug development and quality control in the pharmaceutical industry. Although initially developed for immediate release (IR) solid oral dosage forms and then extended to controlled/modified release solid oral dosage forms, dissolution testing is described as having been widened to a variety of "novel" or "special" dosage forms such as suspensions, orally disintegrating tablets, chewable tablets, chewing gums, transdermal patches, semisolid topical preparations, suppositories, implants and injectable microparticulate formulations, and liposomes.

The Siewert article states that because of significant differences in formulation design among these novel/special dosage forms, which in turn lead to very different physicochemical and release characteristics, it is not possible to devise a single test system that could be used to study the drug release properties of all products. Rather, different apparatus, procedures, and techniques are employed on a case-by-case basis. The method may be specific to the dosage form category, the formulation type, or the particular product.

Alza Corporation (CA, USA) has developed "Macroflux®" products, which are described as incorporating a thin titanium screen with precision microprojections which, when applied to the skin, create superficial pathways through the skin's dead barrier layer allowing transport of macromolecules. Macroflux® products provide the option of dry-coating the drug on the Macroflux® microprojection array for bolus delivery into the skin or using a drug reservoir for continuous passive or electrotransport applications. In addition, the creation of Macroflux® pathways is described as allowing for better control of drug distribution throughout the skin patch treatment area and reduction in potential skin irritation.

pION (MA, USA) manufactures the µDISS Profiler™ which is described as being capable of ranking order intrinsic dissolution, detecting polymorphic changes, following stability profiles, and determining equilibrium solubility.

The following patents and patent applications, relevant portions of which are incorporated herein by reference, may be of interest:

U.S. Pat. No. 6,855,372 to Trautman et al.
US Patent Application Publication 2004/0059282 to Flock et al.
U.S. Pat. No. 5,685,837 to Horstmann
U.S. Pat. No. 5,230,898 to Horstmann et al.
U.S. Pat. No. 6,522,918 to Crisp et al.
U.S. Pat. No. 6,374,136 to Murdock
U.S. Pat. No. 6,251,100 to Flock et al.
US Patent Application Publication 2003/0204163 to Marchitto et al.
U.S. Pat. No. 5,141,750 to Lee et al.
U.S. Pat. No. 6,248,349 to Suzuki et al.
PCT Publication WO 05/088299 to Tsuji et al.

The following articles, relevant portions of which are incorporated herein by reference, may be of interest:

Patel et al., "Fast dissolving drug delivery systems: An update," Pharmainfo.net (July 2006)

Levin et al., "Transdermal delivery of human growth hormone through RF-microchannels," Pharm. Res. 2005 April; 22(4):550-5. Epub 2005 Apr. 7

SUMMARY OF THE INVENTION

In some embodiments of the present invention, the rate of dissolution of drugs on a drug patch is determined. The embodiments are, typically, used with drug patches which comprise a drug side and a back side, the patches being configured to deliver drugs to a subject transdermally, by the drug side being placed against the skin of the subject. The dissolution rate of drugs on the patch is determined to provide an indication of the proportion of the drug on a similarly manufactured patch that will be delivered to a subject.

In some embodiments, one patch out of a batch of patches is placed in the laboratory on top of an absorbent material, the drug side being in contact with the absorbent material. The drug patch and the absorbent material are then squeezed together for a period of time. An indication of the quantity of the drug that dissolved is determined by analyzing the absorbent material.

Typically, the absorbent material is wetted prior to the patch being placed upon the absorbent material. For some applications, the patch and the absorbent material are squeezed together by placing a weight on top of the patch. Alternatively or additionally, the patch and the absorbent material are clamped together.

The contents of the absorbent material are analyzed either by directly analyzing the absorbent material, or by extracting the contents of the absorbent material therefrom and analyzing the extracted contents. For example, the drug which dissolved during the squeezing is extracted from the absorbent material, by shaking the material in a solution. The quantity of drug extracted from the material is then determined using chromatography, spectroscopy, and/or another analytical method. In some embodiments, the absorbent material is analyzed directly using spectroscopy.

There is therefore provided, in accordance with an embodiment of the invention, apparatus for use with a drug on a drug patch, the drug patch including a drug side and a back side, the apparatus including:

a surface;

an absorbent material configured to be disposed on the surface and underneath the drug patch; and a squeezing device having a squeezing surface configured to squeeze the drug patch together with the absorbent material.

In an embodiment, the squeezing device includes a clamp.

In an embodiment, the squeezing device includes a weight configured to be placed on top of the drug patch.

In an embodiment, the weight weighs between 1 gram and 35 grams.

In an embodiment, the weight weighs between 5 grams and 15 grams.

In an embodiment, the weight weighs between 25 grams and 35 grams.

In an embodiment, a weight of the weight per unit area of the drug patch is between 3.5 g/sq cm and 5 g/sq cm.

In an embodiment, a weight of the weight per unit area of the drug patch is between 4.1 g/sq cm and 4.3 g/sq cm.

In an embodiment, a weight of the weight per unit area of the drug patch is between 6 g/sq cm and 7.5 g/sq cm.

In an embodiment, a weight of the weight per unit area of the drug patch is between 6.8 g/sq cm and 7 g/sq cm.

In an embodiment, the apparatus further includes a liquid configured to wet the absorbent material.

In an embodiment, the apparatus includes between 0.5 microliter and 20 microliters of the liquid per square cm of the absorbent material.

In an embodiment, the apparatus includes between 1 microliter and 12 microliters of the liquid per square cm of the absorbent material.

In an embodiment, the apparatus further includes an analysis unit configured to analyze the absorbent material.

In an embodiment, the analysis unit is configured to determine a quantity of the drug dissolved by the absorbent material, by analyzing the absorbent material.

In an embodiment, the analysis unit includes a liquid configured to extract the drug from the absorbent material.

In an embodiment, the liquid includes hydrochloric acid solution.

In an embodiment, the liquid includes phosphate buffer.

In an embodiment, the surface includes a well configured to receive the extracted drug.

In an embodiment, the analysis unit includes a spectrophotometer.

There is also provided, in accordance with an embodiment of the invention, a method for use with a drug on a drug patch, the drug patch including a drug side and a back side, the method including:

placing the drug side of the drug patch on top of an absorbent material;

squeezing the drug patch and the absorbent material together for a period of time; and determining an indication of a quantity of the drug that dissolved in the period of time, by analyzing the absorbent material.

In an embodiment, the method further includes wetting the absorbent material prior to squeezing the drug patch and the absorbent material together.

In an embodiment, squeezing the drug patch and the absorbent material together includes squeezing them together for a period of time that is between 2 and 15 minutes.

In an embodiment, analyzing the absorbent material includes performing a procedure selected from the group consisting of chromatography and spectroscopy.

The present invention will be more fully understood from the following detailed description of embodiments thereof, taken together with the drawings, in which:

DETAILED DESCRIPTION OF EMBODIMENTS

Figure 1:
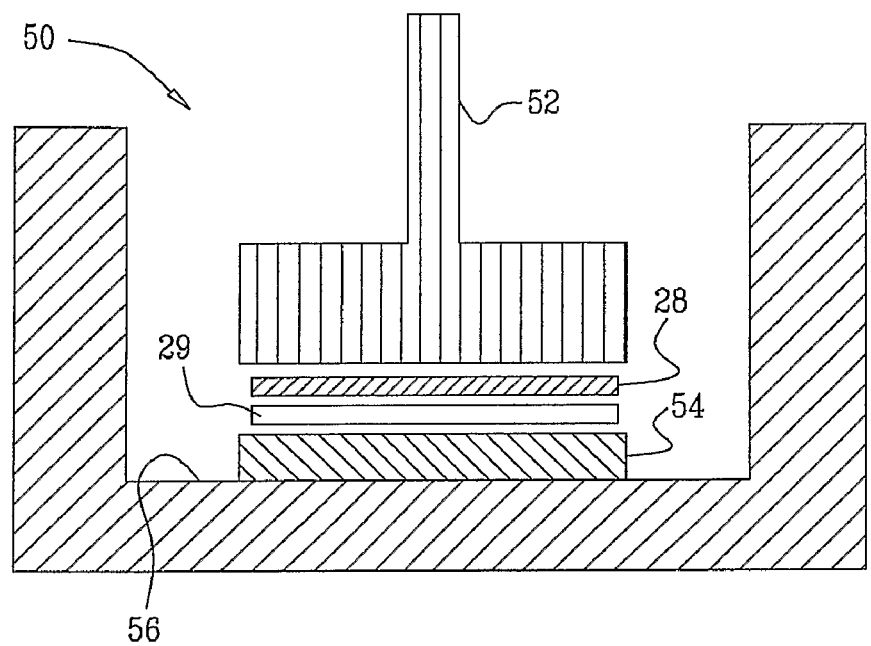
FIG. 1 is a schematic illustration of apparatus for verifying the dissolution properties of a drug patch, in accordance with an embodiment of the invention.

Reference is now made to FIG. 1, which is a schematic illustration of apparatus 50 for verifying the dissolution properties of a drug patch 28, in accordance with an embodiment of the invention. The apparatus is, typically, used with drug patches which comprise a drug side and a back side, the patches being configured to deliver drugs to a subject transdermally, by the drug side being placed against the skin of the subject. Suitable patches are described in the article by Levin et al., and the '132 patent application publication, both of which are cited herein. The dissolution rate of drugs on the patch is determined to provide an indication of the proportion of the drug on a similarly manufactured patch that will be delivered to a subject.

In some embodiments, a piece of absorbent material 54 is placed upon a surface 56 and the drug patch is placed upon the absorbent material. For example, absorbent material 54 may comprise non-woven material, woven material, fabric, a screen, a net, cotton-wool, and/or another type of material. Typically, the absorbent material is wetted, and there is a liquid medium 29 between the absorbent material and the patch (i.e., acting as a bridging interface between the absorbent material and the patch). The liquid is typically in close contact with both the material and the patch. The absorbent material is, typically, wetted with between 0.5 microliter and 20 microliter, for example, between 1 microliter and 12 microliters, of liquid, per square cm of absorbent material. The liquid comprises, for example, phosphate buffer, saline, Dulbecco's phosphate buffered saline (D-PBS), distilled water, Ringer's solution, and/or other buffers. Typically, when used with parathyroid hormone (PTH(1-34)) patches, the absorbent material is wetted with D-PBS, and when used with human growth hormone (hGH) patches, the absorbent material is wetted with 0.025 M phosphate buffer. Typically, hydrophilic liquids, such as those described above, are used for verifying dissolution properties of drug-patches that contain water soluble drugs. In some embodiments, organic solvents are used as liquid medium 29, for verifying dissolution properties of drug patches that contain lipophilic drugs.

In some embodiments, patch 28 and absorbent material 54 are squeezed together by a weight 52, which is placed on top of the back side of the patch. Typically, patch 28 comprises an active drug core and an adhesive backing for adhering the patch to a patient's skin. The rim of the adhesive backing is removed from the patch prior to performing the dissolution verification procedure described herein. The rim is typically cut away using scissors and/or another cutting instrument.

In some embodiments, patch 28 includes a large patch, and weight 52 is a large weight. The large patch is typically circular, having a diameter of 30 mm after the adhesive backing rim has been removed. In such embodiments, weight 52 typically weighs between 25 g and 35 g, e.g., 30 g. Typically, the weight is a round weight with a diameter that is between 3 cm and 4 cm, e.g., 3.3 cm. Typically, the weight per unit area of the patch that is placed on the large patch is between 3.5 g/sq cm and 5 g/sq cm, e.g., between 4.1 g/sq cm and 4.3 g/sq cm.

In some embodiments, patch 28 includes a small patch and weight 52 is a small weight. After removing the rim of the adhesive backing, the small patch is typically a 12 mm by 12 mm square having a 1 square cm active drug core. In such embodiments, weight 52 is round and weighs between 5 g and 15 g, e.g., 10 g. The diameter of the weight is typically between 1.5 cm and 2.5 cm, e.g., 2 cm. Typically, the weight per unit area of the patch that is placed on the small patch is between 6 g/sq cm and 7.5 g/sq cm, e.g., between 6.8 g/sq cm and 7.0 g/sq cm. Typically, the squeezing lasts for between 2 minutes and 15 minutes, although in some embodiments the squeezing lasts for a different period of time. Generally, the period of time for which the squeezing lasts varies in accordance with the formulation of the drug on the drug patch and the formulation of liquid medium 29. Further typically, the squeezing is such that there is complete or near-complete contact between the drug side of the patch and absorbent material 54.

Although drug patches having specific dimensions are described hereinabove, the scope of this invention includes performing the patch dissolution verification techniques described herein on patches having different dimensions. When the techniques are applied to drug patches having different dimensions, the dimensions of the absorbent material, and/or the other apparatus may vary accordingly.

Subsequent to the squeezing, absorbent material 54 is analyzed to determine the quantity of drug which was dissolved by or into the absorbent material during the squeezing. In some embodiments, as shown in FIG. 1, surface 56 comprises a well and the squeezing is performed inside the well. Subsequent to the squeezing, weight 52 and patch 28 are removed from the well. The drug which was dissolved by or into the material is extracted from the material by adding an extraction liquid to the well and shaking the well. Typically, 0.01 M hydrochloric acid solution is used as the extraction liquid with parathyroid hormone (PTH(1-34)) patches and 0.025 M phosphate buffer is used with human growth hormone (hGH) patches. The quantity of the drug dissolved by the patch is determined by analyzing the contents of the well using chromatography. Alternatively or additionally, the quantity of the drug dissolved by the material is determined using spectroscopy, and/or another analytical method.

Figure 2:
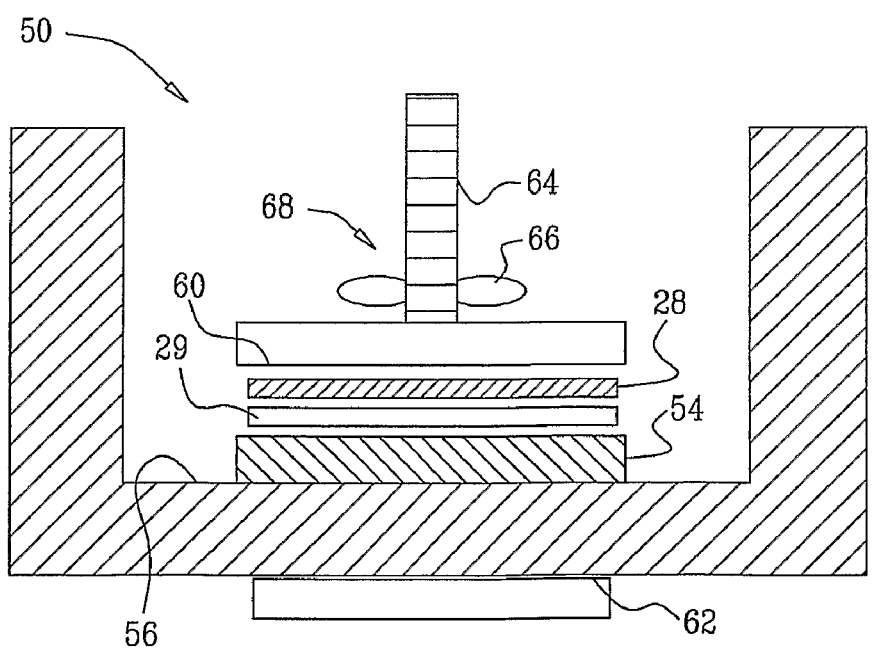
FIG. 2 is a schematic illustration of apparatus for verifying the dissolution properties of a drug patch, in accordance with another embodiment of the invention.

Reference is now made to FIG. 2, which is a schematic illustration of apparatus 50 for verifying the dissolution properties of a drug patch 28, in accordance with another embodiment of the invention. In the embodiment shown, patch 28 is squeezed together with the absorbent material using a clamp 68. The clamp typically comprises an upper squeezing surface 60, a lower squeezing surface 62, a screw rod 64, and a screw nut 66. In all other aspects, the apparatus is generally the same as that described with respect to FIG. 1 above.

EXAMPLES

1) A round non-woven piece of absorbent material having a diameter of 30 mm, and composed of 30% polypropylene, and 70% cellulose (Shalag Industries A.C.S., Ltd.), was wetted with 60 microliters of 0.025 M phosphate buffer with a pH of 7. The absorbent material was placed on a multi-well dish, which had six wells. An hGH patch was placed on the wet piece of absorbent material with the drug side of the patch in contact with the material. Human growth hormone (hGH) patches containing 0.5 mg, 1 mg, 2.0 mg, and 5 mg were analyzed in this experiment. Each patch comprised an adhesive backing liner, a foam raising pad, a printing liner, and a drug layer. The rim of the adhesive backing was removed from the drug patch by cutting it with scissors, leaving a 30 mm diameter round drug core of the drug patch. A 30 g weight was placed upon the back side of the drug patch for 5 minutes. The drug released into the absorbent material was extracted by adding further phosphate buffer to the material and agitating the well by centrifuging the well at 100 rpm for five minutes. The extracted solution was analyzed using high performance liquid chromatography (HPLC).

2) A 12×12 mm square piece of absorbent polyethylene terephthalate net (PET, Sefar, catalog number 140-34W PW) having an open area that is 19.4% of its total area was placed inside a multi-well dish having twelve wells. The open area was wetted with 4 microliters of D-PBS with pH 7.4. A parathyroid hormone (PTH(1-34)) patch was placed drug side down on the PET net, and a 10 g weight was placed on top of the back side of the patch for 5 minutes. The drug released into the PET was extracted by adding 0.5 ml of 0.01 M hydrochloric acid solution and agitating the well by centrifuging the well at 100 rpm for five minutes. The extracted solution was analyzed using HPLC.

Although specific liquids have been described for wetting the absorbent material, and for extracting the contents of the drug patch therefrom, the scope of this invention includes using other liquids for one, or both, of these purposes. Typically, the wetting liquid and the extraction liquid are selected in accordance with the characteristics of the drug contained in the drug patch, for example, the solubility of the drug.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a drug on a drug patch, the drug patch including a drug side and a back side, the apparatus comprising:
   a surface;
   an absorbent material configured to be disposed on the surface and underneath the drug patch; and
   a squeezing device having a squeezing surface configured to squeeze the drug patch together with the absorbent material.

2. The apparatus according to claim 1, wherein the squeezing device comprises a clamp.

3. The apparatus according to claim 1, wherein the squeezing device comprises a weight configured to be placed on top of the drug patch.

4. The apparatus according to claim 3, wherein the weight weighs between 1 gram and 35 grams.

5. The apparatus according to claim 4, wherein the weight weighs between 5 grams and 15 grams.

6. The apparatus according to claim 4, wherein the weight weighs between 25 grams and 35 grams.

7. The apparatus according to claim 4, wherein a weight of the weight per unit area of the drug patch is between 3.5 g/sq cm and 5 g/sq cm.

8. The apparatus according to claim 7, wherein a weight of the weight per unit area of the drug patch is between 4.1 g/sq cm and 4.3 g/sq cm.

9. The apparatus according to claim 4, wherein a weight of the weight per unit area of the drug patch is between 6 g/sq cm and 7.5 g/sq cm.

10. The apparatus according to claim 9, wherein a weight of the weight per unit area of the drug patch is between 6.8 g/sq cm and 7 g/sq cm.

11. The apparatus according to claim 1, further comprising liquid configured to wet the absorbent material.

12. The apparatus according to claim 11, wherein the liquid comprises between 0.5 microliter and 20 microliters of the liquid per square cm of the absorbent material.

13. The apparatus according to claim 12, wherein the liquid comprises between 1 microliter and 12 microliters of the liquid per square cm of the absorbent material.

14. The apparatus according to claim 11, wherein the liquid is also configured to extract a drug from the absorbent material.

15. The apparatus according to claim 14, wherein the liquid comprises hydrochloric acid solution.

16. The apparatus according to claim 14, wherein the liquid comprises phosphate buffer.

17. The apparatus according to claim 14, wherein the surface is a surface of a well configured to receive the extracted drug.

18. A method for use with a drug on a drug patch, the drug patch including a drug side and a back side, the method comprising:
   placing the drug side of the drug patch on top of an absorbent material;
   squeezing the drug patch and the absorbent material together for a period of time; and
   determining an indication of a quantity of the drug that dissolved in the period of time, by analyzing the absorbent material.

19. The method according to claim 18, further comprising wetting the absorbent material prior to squeezing the drug patch and the absorbent material together.

20. The method according to claim 18, wherein squeezing the drug patch and the absorbent material together comprises placing a weight above the back side of the drug patch.

21. The method according to claim 18, wherein squeezing the drug patch and the absorbent material together comprises clamping the drug patch and the absorbent material together.

22. The method according to claim 18, wherein squeezing the drug patch and the absorbent material together comprises squeezing them together for a period of time that is between 2 and 15 minutes.

23. The method according to claim 18, wherein analyzing the absorbent material comprises performing a procedure selected from the group consisting of chromatography and spectroscopy.

* * * * *